US006187759B1

(12) United States Patent
Tarpey et al.

(10) Patent No.: US 6,187,759 B1
(45) Date of Patent: Feb. 13, 2001

(54) CANINE PARVOVIRUS DNA VACCINATION

(75) Inventors: Ian Tarpey; Neil Greenwood, both of St. Ives (GB)

(73) Assignee: Akzo Nobel N.V., Arnhem (NL)

( * ) Notice: Under 35 U.S.C. 154(b), the term of this patent shall be extended for 0 days.

(21) Appl. No.: 09/022,949

(22) Filed: Feb. 12, 1998

(30) Foreign Application Priority Data

Feb. 12, 1997 (EP) .................................................. 97300889

(51) Int. Cl.$^7$ ............................ C12N 15/86; C12N 15/79; A61K 31/70; C07H 21/04
(52) U.S. Cl. ..................... 514/44; 435/320.1; 435/235.1; 536/23.1
(58) Field of Search ............................. 435/235.1, 320.1; 514/44; 424/93.2

(56) References Cited

U.S. PATENT DOCUMENTS

| 5,498,413 | * | 3/1996 | Alvarez et al. | 424/233.1 |
| 5,593,972 | * | 1/1997 | Weiner et al. | 514/44 |
| 5,882,652 | * | 3/1999 | Valdes et al. | 424/221.1 |

FOREIGN PATENT DOCUMENTS

| 0117767 | 9/1984 | (EP) . |
| 0341611 | 11/1989 | (EP) . |
| 0554414 | 8/1993 | (EP) . |
| WO 88/02026 | 3/1988 | (WO) . |
| WO 91/02054 | 2/1991 | (WO) . |
| WO 96/12808 | 5/1996 | (WO) . |
| WO 96/14088 | 5/1996 | (WO) . |
| WO 97/40163 | 10/1997 | (WO) . |
| WO 98/03199 | 1/1998 | (WO) . |
| WO 98/03658 | 1/1998 | (WO) . |
| WO 98/03660 | 1/1998 | (WO) . |

OTHER PUBLICATIONS

J. De Turiso et al., *Journal of Virology*, 66:5:2748–2753, 1992.
McDonnell et al. Molecular Medicine, DNA Vaccines. The New England Journal of Medicine, Vol. 334, pp. 42–45, Jan. 1996.*
Zinkernagel, R. Fundamental Immunology, Paul, W. ed. Chapter 34, 1993.*
Chattergoon et al. Genetic Immunization: A New Era in Vaccines and Immune Therapeutics. FASEB Journal, vol. 11, pp. 753–763, Aug. 1997.*
Hassett et al. Neonatal DNA Immunization with a Plasmid Encoding an Internal Viral Protein Is Effective in the Presence of Maternal Antibodies and Protects against Subsequent Viral Challenge. Journal of Virology, Vol. 71, pp. 7881–7888. Oct. 1997.*
Manickan et al. DNA Immunization of Neonates Induces Immunity Despite the Presence of Maternal Antibody. J. Clinical Investigation, Vol. 100, pp. 2371–2375, Nov. 1997.*

* cited by examiner

*Primary Examiner*—Deborah J. R. Clark
(74) *Attorney, Agent, or Firm*—Michael G. Sullivan

(57) ABSTRACT

This invention relates to the use of a DNA vaccine for the manufacture of a medicament for use in eliciting an immune response against parvovirus in a maternally derived antibody positive animals. The DNA vaccine comprises a plasmid vector and at least one isolated nucleotide sequence encoding a parvovirus immunogenic polypeptide, and transcriptional regulatory sequences operably linked to the isolated nucleotide sequence.

17 Claims, 1 Drawing Sheet

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 1752 base pairs
      (B) TYPE: nucleic acid
      (C) STRANDEDNESS: double
      (D) TOPOLOGY: unknown (ii) MOLECULE TYPE: DNA (genomic)

(xi) SEQUENCE DESCRIPTION: SEQ ID NO: 1:

```
ATGAGTGATG GAGCAGTTCA ACCAGACGGT GGTCAACCTG CTGTCAGAAA TGAAAGAGCT      60

ACAGGATCTG GGAACGGGTC TGGAGGCGGG GGTGGTGGTG GTTCTGGGGG TGTGGGGATT     120

TCTACGGGTA CTTTCAATAA TCAGACGGAA TTTAAATTTT TGGAAAACGG ATGGGTGGAA     180

ATCACAGCAA ACTCAAGCAG ACTTGTACAT TTAAATATGC CAGAAAGTGA AAATTATAGA     240

AGAGTGGTTG TAAATAATTT GGATAAAACT GCAGTTAACG GAAACATGGC TTTAGATGAT     300

ACTCATGCAC AAATTGTAAC ACCTTGGTCA TTGGTTGATG CAAATGCTTG GGGAGTTTGG     360

TTTAATCCAG GAGATTGGCA ACTAATTGTT AATACTATGA GTGAGTTGCA TTTAGTTAGT     420

TTTGAACAAG AAATTTTTAA TGTTGTTTTA AAGACTGTTT CAGAATCTGC TACTCAGCCA     480

CCAACTAAAG TTTATAATAA TGATTTAACT GCATCATTGA TGGTTGCATT AGATAGTAAT     540

AATACTATGC CATTTACTCC AGCAGCTATG AGATCTGAGA CATTGGGTTT TTATCCATGG     600

AAACCAACCA TACCAACTCC ATGGAGATAT TATTTTCAAT GGGATAGAAC ATTAATACCA     660

TCTCATACTG GAACTAGTGG CACACCAACA AATATATACC ATGGTACAGA TCCAGATGAT     720

GTTCAATTTT ATACTATTGA AAATTCTGTG CCAGTACACT TACTAAGAAC AGGTGATGAA     780

TTTGCTACAG GAACATTTTT TTTTGATTGT AAACCATGTA GACTAACACA TACATGGCAA     840

ACAAATAGAG CATTGGGCTT ACCACCATTT CTAAATTCTT TGCCTCAATC TGAAGGAGGT     900

ACTAACTTTG GTTATATAGG AGTTCAACAA GATAAAAGAC GTGGTGTAAC TCAAATGGGA     960
```

-continued

```
AATACAAACT ATATTACTGA AGCTACTATT ATGAGACCAG CTGAGGTTGG TTATAGTGCA    1020

CCATATTATT CTTTTGAGGC GTCTACACAA GGGCCATTTA AAACACCTAT TGCAGCAGGA    1080

CGGGGGGGAG CGCAAACAGA TGAAAATCAA GCAGCAGATG GTGATCCAAG ATATGCATTT    1140

GGTAGACAAC ATGGTCAAAA AACTACCACA ACAGGAGAAA CACCTGAGAG ATTTACATAT    1200

ATAGCACATC AAGATACAGG AAGATATCCA GAAGGAGATT GGATTCAAAA TATTAACTTT    1260

AACCTTCCTG TAACAAATGA ATAATGTATTG CTACCAACAG ATCCAATTGG AGGTAAAACA    1320

GGAATTAACT ATACTAATAT ATTTAATACT TATGGTCCTT TAACTGCATT AAATAATGTA    1380

CCACCAGTTT ATCCAAATGG TCAAATTTGG GATAAAGAAT TTGATACTGA CTTAAAACCA    1440

AGACTTCATG TAAATGCACC ATTTGTTTGT CAAAATAATT GTCCTGGTCA ATTATTTGTA    1500

AAAGTTGCGC CTAATTTAAC AAATGAATAT GATCCTGATG CATCTGCTAA TATGTCAAGA    1560

ATTGTAACTT ACTCAGATTT TTGGTGGAAA GGTAAATTAG TATTTAAAGC TAAACTAAGA    1620

GCCTCTCATA CTTGGAATCC AATTCAACAA ATGAGTATTA ATATAGATAA CCAATTTAAC    1680

TATGTACCAA GTAATATTGG AGGTATGAAA ATTGTATATG AAAAATCTCA ACTAGCACCT    1740

AGAAAATTAT AT                                                        1752
```

(2) INFORMATION FOR SEQ ID NO: 2:

(i) SEQUENCE CHARACTERISTICS:
        (A) LENGTH: 584 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

```
Met Ser Asp Gly Ala Val Gln Pro Asp Gly Gly Gln Pro Ala Val Arg
1               5                   10                  15

Asn Glu Arg Ala Thr Gly Ser Gly Asn Gly Ser Gly Gly Gly Gly
            20                  25                  30

Gly Gly Ser Gly Gly Val Gly Ile Ser Thr Gly Thr Phe Asn Asn Gln
        35                  40                  45

Thr Glu Phe Lys Phe Leu Glu Asn Gly Trp Val Glu Ile Thr Ala Asn
    50                  55                  60

Ser Ser Arg Leu Val His Leu Asn Met Pro Glu Ser Glu Asn Tyr Arg
65                  70                  75                  80

Arg Val Val Val Asn Asn Leu Asp Lys Thr Ala Val Asn Gly Asn Met
                85                  90                  95

Ala Leu Asp Asp Thr His Ala Gln Ile Val Thr Pro Trp Ser Leu Val
                100                 105                 110

Asp Ala Asn Ala Trp Gly Val Trp Phe Asn Pro Gly Asp Trp Gln Leu
            115                 120                 125

Ile Val Asn Thr Met Ser Glu Leu His Leu Val Ser Phe Glu Gln Glu
        130                 135                 140

Ile Phe Asn Val Val Leu Lys Thr Val Ser Glu Ser Ala Thr Gln Pro
145                 150                 155                 160

Pro Thr Lys Val Tyr Asn Asn Asp Leu Thr Ala Ser Leu Met Val Ala
                165                 170                 175

Leu Asp Ser Asn Asn Thr Met Pro Phe Thr Pro Ala Ala Met Arg Ser
                180                 185                 190

Glu Thr Leu Gly Phe Tyr Pro Trp Lys Pro Thr Ile Pro Thr Pro Trp
```

-continued

```
            195                 200                 205
Arg Tyr Tyr Phe Gln Trp Asp Arg Thr Leu Ile Pro Ser His Thr Gly
    210                 215                 220

Thr Ser Gly Thr Pro Thr Asn Ile Tyr His Gly Thr Asp Pro Asp Asp
225                 230                 235                 240

Val Gln Phe Tyr Thr Ile Glu Asn Ser Val Pro Val His Leu Leu Arg
                245                 250                 255

Thr Gly Asp Glu Phe Ala Thr Gly Thr Phe Phe Phe Asp Cys Lys Pro
                260                 265                 270

Cys Arg Leu Thr His Thr Trp Gln Thr Asn Arg Ala Leu Gly Leu Pro
                275                 280                 285

Pro Phe Leu Asn Ser Leu Pro Gln Ser Glu Gly Thr Asn Phe Gly
    290                 295                 300

Tyr Ile Gly Val Gln Gln Asp Lys Arg Arg Gly Val Thr Gln Met Gly
305                 310                 315                 320

Asn Thr Asn Tyr Ile Thr Glu Ala Thr Ile Met Arg Pro Ala Glu Val
                325                 330                 335

Gly Tyr Ser Ala Pro Tyr Tyr Ser Phe Glu Ala Ser Thr Gln Gly Pro
                340                 345                 350

Phe Lys Thr Pro Ile Ala Ala Gly Arg Gly Gly Ala Gln Thr Asp Glu
                355                 360                 365

Asn Gln Ala Ala Asp Gly Asp Pro Arg Tyr Ala Phe Gly Arg Gln His
    370                 375                 380

Gly Gln Lys Thr Thr Thr Thr Gly Glu Thr Pro Glu Arg Phe Thr Tyr
385                 390                 395                 400

Ile Ala His Gln Asp Thr Gly Arg Tyr Pro Glu Gly Asp Trp Ile Gln
                405                 410                 415

Asn Ile Asn Phe Asn Leu Pro Val Thr Asn Asp Asn Val Leu Leu Pro
                420                 425                 430

Thr Asp Pro Ile Gly Gly Lys Thr Gly Ile Asn Tyr Thr Asn Ile Phe
    435                 440                 445

Asn Thr Tyr Gly Pro Leu Thr Ala Leu Asn Asn Val Pro Pro Val Tyr
    450                 455                 460

Pro Asn Gly Gln Ile Trp Asp Lys Glu Phe Asp Thr Asp Leu Lys Pro
465                 470                 475                 480

Arg Leu His Val Asn Ala Pro Phe Val Cys Gln Asn Asn Cys Pro Gly
                485                 490                 495

Gln Leu Phe Val Lys Val Ala Pro Asn Leu Thr Asn Glu Tyr Asp Pro
                500                 505                 510

Asp Ala Ser Ala Asn Met Ser Arg Ile Val Thr Tyr Ser Asp Phe Trp
                515                 520                 525

Trp Lys Gly Lys Leu Val Phe Lys Ala Lys Leu Arg Ala Ser His Thr
    530                 535                 540

Trp Asn Pro Ile Gln Gln Met Ser Ile Asn Ile Asp Asn Gln Phe Asn
545                 550                 555                 560

Tyr Val Pro Ser Asn Ile Gly Gly Met Lys Ile Val Tyr Glu Lys Ser
                565                 570                 575

Gln Leu Ala Pro Arg Lys Leu Tyr
                580
```

CANINE PARVOVIRUS DNA VACCINATION

FIELD OF THE INVENTION

The present invention relates to a DNA vaccine for stimulating protective immunity in animals against a parvovirus. More specifically, the present invention relates to the use of a DNA vaccine for eliciting an immune response against parvovirus in maternally derived antibody (MDA) positive animals. In particular, it relates to the use of a DNA vaccine for eliciting an immune response against canine parvovirus (CPV) in MDA positive dogs. The invention also relates to a plasmid vector suitable for use in a DNA vaccine against parvovirus, in particular canine parvovirus.

BACKGROUND OF THE INVENTION

CPV is primarily an enteric pathogen of CANIDAE. It causes an infection in dogs, especially young dogs, which frequently leads to an enteric disease characterised by acute diarrhoea, fever and leukopenia. It can cause high mortality/high morbidity in infected animals. CPV is genetically and antigenically closely related to Feline panleukopenia virus (FPV), Mink enteritis virus (PEV), Raccoon parvovirus (RPV) and is considered to be a host range variant of one of these viruses.

Vaccines have been developed to prevent parvoviral infection of target animals such as dogs, cats, mink, raccoon, and cattle, in particular dogs and cats. CPV and FPV can be effectively controlled by vaccination with live attenuated CPV and FPV, respectively. Puppies can be protected when maternally derived antibodies are present, by specially developed live attenuated vaccines only, such as described for example in WO 9102054. Such vaccines suffer from the disadvantage that modified live vaccine virus could be excreted post vaccination. The use of an inactivated, adjuvanted preparation, however, may be regarded as safer as no live virus can be excreted post vaccination. Higher concentrations of inactivated vaccine are required to stimulate an antibody response, particularly in the presence of maternally derived antibody (MDA). However, the presence of high titres of MDA can prevent effective vaccination with inactivated vaccines.

In some puppies the passive immunity to certain antigens can persist for a considerable period (4 months or more) at levels sufficient to interfere with vaccination. As the MDA level declines a puppy may be protected insufficiently against infection and disease, but still be refractory to vaccination. Hence, these puppies remain unprotected during a considerable period in their early life. The danger of infection of complete litters poses a serious risk, particularly after the maternally derived immunity has vanished. The potential risk of infection due to the presence of MDA was known for dogs, but has recently been recognized to affect certain neonates of other animals as well, in particular in MDA positive offspring of cats, minks and raccoons.

Recent developments in the vaccine field have resulted in a novel class of vaccines based on the induction of immunity following the delivery of plasmid DNA encoding immunogenic proteins. Such vaccines may hold the promise of protecting against disease by inducing both humoral and cell-mediated immune response, without many of the disadvantages associated with vaccines presently in use.

Whilst it was hoped that the efficacy of DNA immunization would not be reduced by maternally derived antibodies, in practice it has been found that vaccination of one-day-old piglets against pseudorabies, using plasmid DNA incorporating the gD glycoprotein gene of pseudorabies, did not result in significant protection. Piglets from immune sows neither developed an antibody response, nor were primed against pseudorabies virus, as demonstrated by the antibodies kinetics after challenge (see Monteil, M. et al., Vet. Res. (1996), 27, 443–452).

In a recent abstract it has been briefly reported that "immunization of dogs with a range of doses of a plasmid encoding the major capsid proteins of canine parvovirus (VP-1, VP-2) resulted in the dose dependent appearance of anti-parvovirus antibodies at significant levels". From the subsequent challenge of the dogs, with a mixture of virulent parvovirus strains, it was evident that all immunized dogs were protected against infection and disease. No mention was made in the abstract of the nature of the construct used. Furthermore, there was no reference to the age of the dogs and their immune status.

One of the main limitations of vaccination concerns the vaccination of the young offspring of immune females. In all species the existence of maternal antibodies is a strong limitation which impairs the development of an immune response in the young.

SUMMARY OF THE INVENTION

It has now been found that use of a DNA molecule comprising a vector, preferably a plasmid vector, and at least one isolated nucleotide sequence encoding a parvovirus polypeptide and transcriptional regulatory sequences operably linked to the isolated nucleotide sequence, will successfully immunize puppies earlier in their lives, even in the face of maternally derived antibody. The present invention thus provides for a new and effective method to vaccinate MDA positive animals against parvoviral infections. The DNA molecule according to the invention can be used to facilitate a DNA vaccine to protect for example, dogs from CPV infections, cats from FPV infections and minks from MEV infections.

Further to the unexpected advantage of vaccination of animals in the face of maternally derived antibodies, the present invention provides for a method of vaccination of MDA positive animals that is not restricted by the host range of the corresponding parvovirus. The DNA molecule can be succesfully used in a broad range of MDA positive animals, because it is not limited by cell tropism, as is the case with live virus vaccines. For example, in case the DNA molecule encodes a CPV immunogenic protein, said DNA molecule can be used in vaccination of not only MDA positive dogs, but animals that are host to parvoviruses that are genetically and antigenically closely related to CPV, e.g. FPV, MEV, and RPV, as well.

Maternally derived antibody (MDA) is passively transferred from a seropositive mother to her offspring, who are passively protected during the first few weeks of life by this circulating MDA. It has been calculated that the neonate receives approximately 90% of its MDA via the colostrum, whereas transplacental transfer accounts for only 10% of the total passive antibody. The range of MDA will vary from neonate to neonate, the weaklings or runts often having the lowest MDA levels due to reduced suckling capabilities or opportunities. The "average" neonate soon after birth will have a serum antibody level equal to 50% that of its mother. This MDA proceeds to decline exponentially with a half-life of approximately 10 days.

For example, pups born to bitches with average humoral antibody titers of 1:2560 (HAI) would be expected to contain MDA with titers in the range of 1:1280 during their first week of life. At approximately 7 weeks of age this antibody titer would decline to 1:20–1:40 which is below protective levels but still high enough to prevent most conventional vaccines working. Most puppies (more than 90%) will contain MDA until at least 10 weeks of age. In the field, in contrast to laboratory bred dogs, most dams are immune as a result of previous exposure to field virus or vaccination, therefore puppies of 10 weeks of age or younger born to immune bitches, are considered to be MDA positive. In particular, puppies of 8 weeks of age or younger born to immune mothers are considered as MDA positive dogs that can be protected by the DNA vaccine described herein.

DESCRIPTION OF THE SEQUENCES

Figure 1:
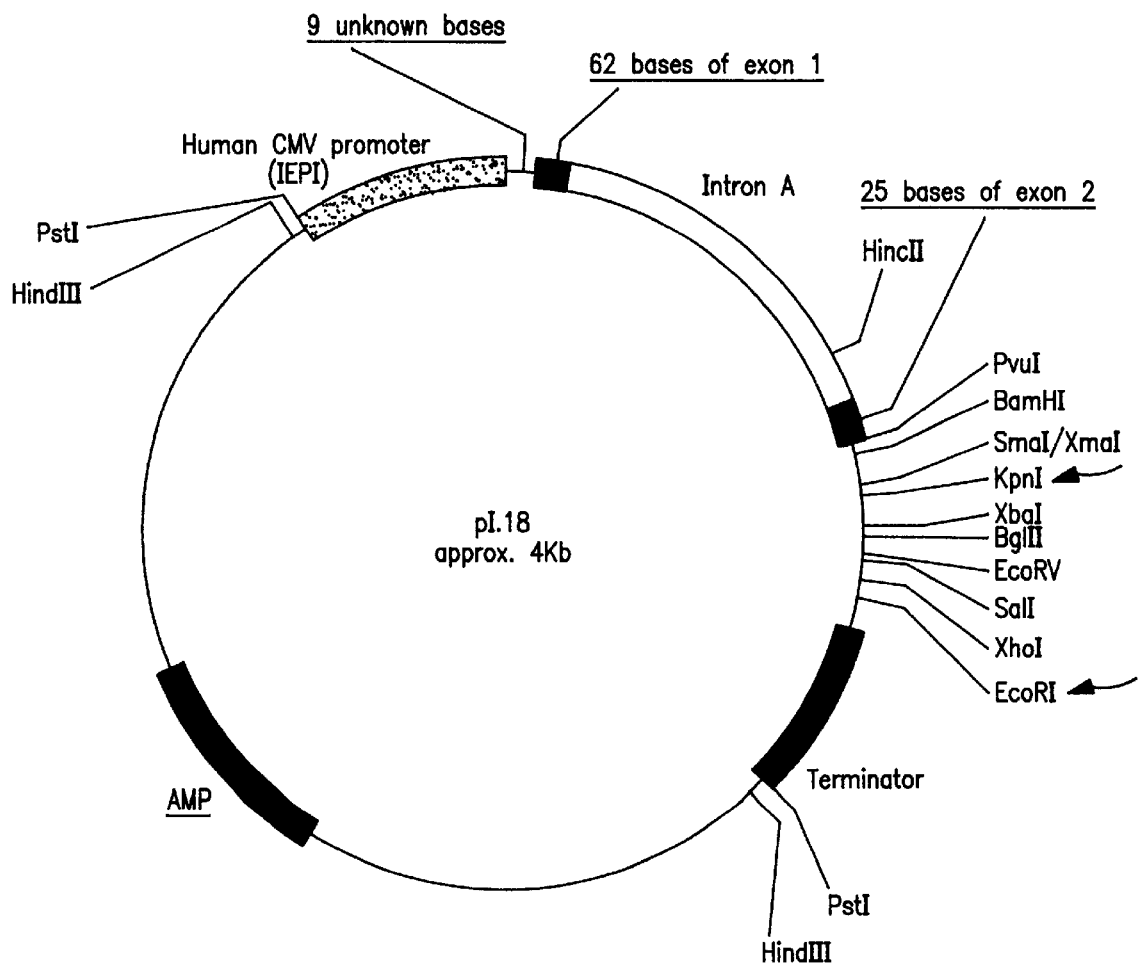
FIG. 1 is a schematic representation of plasmid pI 18.

SEQ ID No.'s: 1 and 2 represent the DNA sequence and the amino acid sequence of a CPV type 2a VP2 gene and protein, respectively.

DETAILED DESCRIPTION OF THE INVENTION

According to one aspect of the invention there is provided the use of a DNA molecule for the manufacture of a medicament for use in eliciting an immune response against parvovirus in a maternally derived antibody positive animal, said DNA molecule comprising a plasmid vector and at least one isolated nucleotide sequence encoding a parvovirus immunogenic polypeptide and transcriptional regulatory sequences operably linked to the isolated nucleotide sequence.

Preferably, the invention provides for the use of a DNA molecule for the manufacture of a medicament for use in eliciting an immune response against canine parvovirus and antigenically closely related parvoviruses in a maternally derived antibody positive animal, said DNA molecule comprising a plasmid vector and at least one isolated nucleotide sequence encoding a CPV immunogenic polypeptide and transcriptional regulatory sequences operably linked to the isolated nucleotide sequence.

More preferably, the invention provides for the use of a DNA molecule for the manufacture of a medicament for use in eliciting an immune response against canine parvovirus in a maternally derived antibody positive dog, said DNA molecule comprising a plasmid vector and at least one isolated nucleotide sequence encoding a CPV immunogenic polypeptide and transcriptional regulatory sequences operably linked to the isolated nucleotide sequence.

The isolated parvoviral nucleotide sequence according to the invention to be used in the DNA molecule for the manufacture of a medicament for use in eliciting an immune response preferably is selected from CPV, FPV, MEV or RPV, more preferably CPV or FPV. Particularly preferred is a CPV nucleotide sequence. Particularly preferred is a CPV nucleotide sequence selected from CPV types 2, 2a and 2b.

Preferably, the isolated parvoviral nucleotide sequence to be used according to the invention codes for the VP2 protein. More preferably, the isolated parvoviral nucleotide sequence is a CPV nucleotide sequence which codes for the VP2 protein of CPV. In particular, the isolated nucleotide sequence has a nucleotide sequence encoding a polypeptide having an amino acid sequence as depicted in SEQ ID NO 2. More particularly, the nucleotide sequence has the nucleotide sequence as shown in SEQ ID NO 1.

The DNA molecule according to the invention may contain more than one isolated nucleotide sequence encoding a parvoviral polypeptide. Thus, for example, in addition to the parvoviral polypeptide encoding a VP2 protein the DNA molecule may in addition contain the nucleotide sequence coding for parvoviral VP1 protein, preferably a CPV VP1 protein. Alternatively, said DNA molecule may contain isolated sequences coding for VP2 proteins from more than one type of parvovirus, whereby said parvoviruses are either selected from different species, e.g. CPV and FPV, or are selected from different types (strains) within a specific species, e.g. CPV types 2, 2a and 2b. Examples of such CPV nucleotide- and amino acid sequences are published by Parrish, C. R. et al., Virology 166, 293–307, 1988; Truyen, U. et al., J. Virology 69, 4702–4710, 1995 and Reed, A. P. et al., J. Virology 62, 266–276, 1988.

In yet another alternative according to the invention, the vector may additionally contain one or more nucleotide sequences encoding a protein from another pathogen. Preferably, said other pathogens are selected from canine-, feline-, and muscelid pathogens. Suitable nucleotide sequences encoding a protein from other canine pathogens that may be incorporated in the plasmid are e.g. the canine distemper virus fusion and/or haemagglutination gene, the canine parainfluenza gene, the rabies G gene, the adenovirus hexon gene, the canine corona spike gene, the canine corona nucleoprotein gene. Suitable nucleotide sequences encoding a protein from feline pathogens that may be incorporated in the plasmid are nucleotide sequences encoding an immunogenic protein from e.g. FIV, FHV, FeLV, FIP, FCV, and the like. Furthermore, a gene encoding a protein that amplifies the immune response to the encoded parvoviral protein, such as a cytokine, may also be incorporated into the plasmid.

Transcriptional regulatory sequences which are operably linked to the isolated parvoviral sequence may be of homologous- or heterologous origin. By homologous is understood that the transcriptional regulatory sequences and the nucleotide sequence are derived from a parvovirus, preferably the same parvovirus. If the transcriptional regulatory sequences are not derived from a parvoviral species, they are of heterologous origin. Preferably the plasmid comprises transcriptional regulatory sequences of heterologous origin. Thus, for example, if the plasmid comprises one or more CPV nucleotide sequences, the transcriptional regulatory sequences are preferably of non-CPV origin. The CPV transcriptional regulatory sequences include the homologous P3.5 and the P38 promoters.

Examples of such heterologous transcriptional regulatory sequences comprise promoters such as the (human) cytomegalovirus immediate early promoter (Seed, B. et al., Nature 329, 840–842, 1987; Fynan, E. F. et al., PNAS 90, 11478–11482, 1993; Ulmer, J. B. et al., Science 259, 1745–1748, 1993), Rous sarcoma virus LTR (RSV, Gorman, C. M. et al., PNAS 79, 6777–6781, 1982; Fynan et al., supra; Ulmer et al., supra), the MPSV LTR (Stacey et al., J. Virology 50, 725–732, 1984), SV40 immediate early promoter (Sprague J. et al., J. Virology 45, 773 ,1983), the metallothionein promoter (Brinster, R. L. et al., Nature 296, 39–42, 1982), the major late promoter of Ad2, the β-actin promoter (Tang et al., Nature 356, 152–154, 1992).

The regulatory sequences may also include terminator and polyadenylation sequences. Amongst the sequences that can be used are the well known bovine growth hormone polyadenylation sequence, the SV40 polyadenylation sequence, the human cytomegalovirus (hCMV) terminator and polyadenylation sequences.

In principle, any transcriptional regulatory sequence can be used that is able to regulate the transcription of a gene in eukaryotic cells as for example described in Sambrook et al, Molecular Cloning, a Laboratory Manual, second edition, Cold Spring Harbor Laboratory Press, 1989. In addition, the regulatory sequences may include an intron, for example, hCMV intron A (Chapman, B. S. et al., Nucleic Acid Research 19, 3979–3986, 1991), the effect of which is to increase the expression of the encoded protein.

Vectors that may be used in the parvoviral DNA vaccine, in particular the CPV DNA vaccine contain a carrier DNA fragment and a suitable expression cassette including transcriptional regulatory sequences, the target gene and other regulatory sequences, if desired. Examples of suitable vectors include pBR322, pUC18 and pUC19, pNeo, pSVL, pMSG (commercially available from Pharmacia Biotech) and pMC1neo, pSG5, pXT1 and pBX (commercially available from Stratagene).

The vector that was used in the present invention was plasmid pI 18. This plasmid was derived from plasmid pI 17 obtained from Dr. J. Robertson (NIBSC) without restriction. This vector, which is believed to be pUC based, had had the hCMV promoter and—intron A and a terminator sequence cloned into it. A multiple cloning site was cloned into plasmid pI 17 resulting in plasmid pI 18.

The entire coding sequence of the canine VP2 gene, 1755 bp (SEQ ID NO.: 1), was cloned into plasmid pI 18 resulting in plasmid vector VP2/pI 18. This plasmid was deposited on Jan. 28, 1997 with the European Collection of Animal Cell Culture, Porton Down, United Kingdom, under the Budapest Treaty and designated accession no. 97012801.

Similar techniques can be used to clone an isolated nucleotide sequence coding for a parvoviral protein into a suitable plasmid, e.g. PI 18, to produce a DNA molecule according to the invention.

According to a second aspect of the invention there is provided a plasmid vector comprising the DNA sequence coding for the VP2 gene of CPV type 2a characterised by deposit no. 97012801 deposited at European Collection of Animal Cell Cultures, Porton Down, UK.

The deposited plasmid vector may be used as a DNA molecule for the manufacture of a medicament for use in eliciting an immune response against canine parvovirus and antigenically closely related parvoviruses in a maternally derived antibody positive animal. Preferably the deposited plasmid vector may be used as a DNA molecule for the manufacture of a medicament for use in eliciting an immune response against CPV, FPV, MEV and/or RPV in a maternally derived antibody positive animal, preferably a dog, cat, mink or raccoon. In particular, the deposited plasmid vector may be used as a DNA molecule for the manufacture of a medicament for use in eliciting an immune response against CPV in a maternally derived antibody positive dog.

According to another aspect of the invention there is provided a parvovirus DNA vaccine for use in immunizing maternally derived antibody positive animals. Preferably the invention provides for a canine parvovirus DNA vaccine for use in immunizing maternally derived antibody positive animals against CPV, FPV, MEV and RPV, respectively. More preferably, the invention provides for a canine parvovirus DNA vaccine for use in immunizing maternally derived antibody positive dogs. In a particular aspect of the invention the DNA vaccines provided for and described above comprise the plasmid vector deposited with the European Collection of animal Cell Cultures, Porton Down, UK and characterized by deposit no. 97012801.

The term "immune response" refers herein to a cellular immune response, such as for example a cytotoxic T-cell response, and humoral response, such as for example increased serum levels of antibodies specific for an antigen or to the presence of neutralising antibodies to an antigen.

By the term "transcriptional regulatory sequences" is meant nucleotide sequences positioned adjacent to a DNA coding sequence which direct transcription of a coding sequence (i.e. facilitate the production of, e.g. CPV VP2 or VP1 protein). The regulatory nucleotide sequences include any sequences which promote sufficient expression of a desired coding sequence (such as VP2 or VP1) and presentation of the protein product to the inoculated animal's immune system such that protective immunity is provided.

The term "promoter" herein refers to a minimal sequence sufficient to direct transcription. The plasmid vector described above may also comprise an enhancer sequence which may or may not be contiguous with the promoter sequence. Enhancer sequences influence promoter-dependent gene expression and may be located in the 5' or 3' regions of the native gene. Expression is constitutive or inducible by external signals or agents. Optionally, expression is cell-type specific, tissue-specific or species specific.

Preparation of Plasmid Vector—VP2/pI. 18

Virus CPV UK 10194, antigenic type 2a, was grown on the $A_{72}$ cell line and double stranded replicative form DNA isolated by Hirt extraction as described by McMaster et al. (J. Virology 38, 368, 1981). The entire coding sequence of the VP2 gene, 1755 bp, was amplified by the Polymerase chain reaction using sense and antisense oligonucleotide primers of the VP2 5' and 3' terminal sequences. To enable ease of subsequent cloning, a KpnI restriction site was added to the sense oligonucleotide and a EcoRI restriction site added to the antisense oligonucleotide.

The PCR products were electrophoresed on an agarose gel and a 1.7 Kb fragment purified. The purified fragment was digested with KpnI and EcoRJ and ligated into the KpnI and EcoRi sites of plasmid vector pI.18. The ligation reaction was transformed by electroporation, into the bacterial host DH5 alpha. The transformation mix was spread onto L agar—ampicillin plates, incubated at 37° C., colonies picked and grown in L broth (containing ampicillin). "Mini prep" DNAs were made and positive clones containing the VP2 gene were identified by restriction enzyme analysis.

A positive clone, designated VP2-pI-18 was amplified in multiple 500 ml L broth cultures and plasmid DNA purified on qiagen giga columns. pI.18 plasmid vector DNA was similarly purified from large L broth cultures. The yield and purity of DNAs was determined spectrophotometrically and by gel electrophoresis. The recombinant VP2 pI.18 and plasmid vector pI.18 were diluted in Dulbecco's phosphate buffered saline.

Determination of VP2 Expression in $A_{72}$ Cells

Approximately 1 μg of pI.18 DNA was transfected into $A_{72}$ cells by electroporation. Transfected cells were seeded, 200 ul of $2 \times 10^5$ cells/ml, onto a 96 well plate and maintained on Wellcome modified Eagle's medium. After 24 hours incubation at 37° C. the medium was removed and cells fixed with cold absolute ethanol for 2 hours at −18° C. The ethanol was removed and cells incubated for one hour at 37° C. with mAb CPV/15/1/C+E/2 (ascitic fluid) followed by incubation for one hour at 37° C. with anti mouse FITC conjugate (containing Evans Blue counter stain). Cells were washed three times with PBS after each incubation step. Expression of VP2 was identified as an intense fluorescence associated with the $A_{72}$ cell nucleic.

The plasmid vector containing at least an isolated CPV nucleotide sequence together with transcriptional regulatory sequences can be administered to an individual, or inoculated, in the presence of adjuvants or other substances that have the capability of promoting DNA uptake or recruiting immune system cells to the site of the inoculation. It should be understood that the CPV DNA itself is expressed in the host cell by transcription factors provided by the host cell, or provided by the plasmid vector.

An individual can be inoculated through any parenteral route, for example, by the intravenous, intraperitoneal, intradermal, subcutaneous, inhalation or intramuscular route. Muscle is a useful site for the delivery and expression of DNA vaccines because animals have a proportionately large muscle mass which is conveniently accessed by direct injection through the skin. A comparatively large dose of DNA vaccine can be deposited into muscle by multiple and/or repetitive injections, for example to extend protection over long periods of time.

Alternatively, the DNA vaccine may be administered by injection to the epidermis, or via the mucosal route by such methods as nose-drops.

No special formulations are necessary for DNA vaccines. Any appropriate physiologically compatible medium is suitable for introducing the DNA vaccine into an individual, such as saline for an injection.

The effective DNA dosage for administration in injectable form will generally be in the range of 50 μg/kg to 1 mg/kg. Booster vaccination may be administered at yearly intervals in order to maintain protection.

According to yet a further aspect of the invention there is provided a method for protecting maternally derived antibody positive animals against parvoviral infections, in particular CPV, FPV, MEV and RPV, comprising administering a DNA vaccine as heretofore described to susceptible animal. More preferably, there is provided a method for protecting maternally derived antibody positive dogs against CPV comprising administering a DNA vaccine as heretofore described to susceptible dogs.

The invention is illustrated by the following examples.

EXAMPLE 1

Study to determine immunogenicity and efficacy of VP2/pI.18 DNA construct in dogs to protect against challenge with wild type CPV2b.

Thirteen beagle puppies, aged 8–9 weeks of age, were divided into 2 groups of 5 dogs and one group of 3 dogs. Five dogs in Group 1 were each inoculated intramuscularly (I/M) with a total dose of 3 mg VP2/pI.18 DNA; 5 dogs in Group 2 were each inoculated (I/M) with a total dose of 1 mg VP2/pI.18 DNA and 3 dogs in Group 3 were inoculated (I/M) with a total dose of 3 mg pI.18 DNA (placebo). All dogs were vaccinated in both quadriceps and biceps femorus muscles, using an inocular concentration of 1 mg/ml. Dogs in Groups 1 and 3 were each given 0.75 ml per muscle, giving a total dose of 3 mg, whilst the dogs in Group 2 were given 0.25 ml per muscle giving a total dose of 1 mg.

Haemagglutination Inhibition Assay

This assay was performed as described.

Dogs were bled prior to vaccination and 21 days post vaccination.

Results

Clinical Observations

All dogs remained clinically normal throughout the 21-day post vaccination observation period. No local reactions were observed at sites of inoculation nor were any pyrexia responses detected.

Serology Results

The results of the HAI test are tabulated below. All pups were bled 14 days prior to vaccination to determine MDA levels. All blood samples were taken at time of vaccination so titres have been extrapolated.

| | | | HM titres (reciprocal) | |
|---|---|---|---|---|
| Group | Dog No. | Vaccine | Pre bleed | Post vaccination |
| 1 | 1 | VP2/pI.18 | <1:4 | 1:320 |
| | 2 | 3 mg per dose | 1:8 | 1:320 |
| | 4 | | 1:4 | 1:320 |
| | 7 | | 1:16 | 1:320 |
| | 9 | | 1:16 | 1:320 |
| 2 | 11 | VP2/pI.18 | 1:16 | 1:320 |
| | 12 | 1 mg per dose | 1:8 | 1:320 |
| | 13 | | 1:16 | 1:320 |
| | 14 | | 1:8 | 1:320 |
| | 15 | | 1:33 | 1:160 |
| 3 | 3 | pI.18 | 1:16 | <1:10 |
| | 5 | 3 mg per dose | 1:4 | <1:10 |
| | 8 | (controls) | 1:8 | <1:10 |

The results show that both groups of vaccinated dogs produced haemagglutination antibody to CPV VP2 to the same degree. All placebo-vaccinated dogs remained antibody negative to CPV. The maternally derived antibody levels in vaccinated dogs were calculated to range from <1:4 (negative) to 1:33.

Conclusion

This study has shown that vaccination of CPV VP2 inserted into plasmid vector pI.18 successfully stimulated an antibody response in young dogs even in the face of MDA (see dogs 7, 9, 11, 13 and 15). No adverse reactions were observed in any dogs post vaccination.

The sero-responses of the VP2 vaccinated dogs were above the minimum protective titre of 1:80 quoted by many authorities (Carmichael, L. E., Proceedings WSAVA Congress 1996, p. 252–258). In marked contrast, all 3 placebo vaccinated animals, kept in the same holding quarters as the Group I dogs (3 mg—VP2) remained antibody negative, indicating that no wild or vaccinal CPV was present.

This novel vaccine has the advantage over conventional vaccines in that it stimulates fully protective antibody titres which should both prevent disease and infection, and that the vaccine will not spread to in-contact animals and so the risk of reversion to virulence cannot occur.

EXAMPLE 2

Study to determine immunogenicity and efficacy of VP2/PI.18 DNA construct in MDA positive dogs to protect against challenge with wild type CPV2b.

Ten beagle puppies, aged 5–6 weeks of age, were divided into 2 groups of 5 dogs. Five dogs in Group 1 were each inoculated intramuscularly (I/M) with a total dose of 1 mg/pI.18 DNA (placebo); 5 dogs in Group 2 were each inoculated (I/M) with a total dose of 1 mg VP2/PI.18 DNA (0.25 per muscle). All dogs in Group 2 were vaccinated in both quadriceps and biceps femorus muscles (0.25 per muscle) using an inoculum concentration of 1 mg/ml. Dogs in Groups 1 were each given 1 ml per muscle, giving a total dose of 1 mg.

Haemagglutination Inhibition Assay

This assay was performed as described.

Dogs were bled prior to vaccination and 7, 14 and 21 days post vaccination.

Results

Clinical Observations

All dogs remained clinically normal throughout the 21-day post vaccination observation period. No local reactions were observed at sites of inoculation nor were any pyrexia responses detected.

Serological Results

The results of the HAI test were tabulated below. All pups were bled on day of vaccination to determine MDA levels and thereafter, 7, 14 and 21 days post vaccination.

| Group | Dog No. | Vaccine | HAI titres (reciprocal) | | |
|---|---|---|---|---|---|
| | | | Pre bleed | Post vaccination | |
| | | | | 7 | 14 |
| 1 | 21 | pI.18 | 64 | 8 | 16 |
| | 22 | 1 mg per | 32 | 16 | 8 |
| | 23 | dose | 64 | 16 | 16 |
| | 24 | (placebo) | 64 | 16 | 16 |
| | 25 | | 64 | 32 | 8 |
| 2 | 26 | VP2/pI.18 | 32 | 16 | 512 |
| | 27 | 1 mg per | 128 | 64 | 256 |
| | 28 | dose | 64 | 32 | 512 |
| | 29 | | 64 | <4 | 1024 |
| | 30 | | 64 | <4 | 512 |

The results show that the vaccinated pups (Group 2) with significant MDA titres ranging from 1:32–1:128 showed an initial half life decline in antibody titre 7 days post vaccination but then developed active antibody by 14 days post vaccination, titres reaching levels of 1:1024. All titres at day 14 p.v. were well above the protective level. The placebo dogs showed decline of MDA.

What is claimed is:

1. A method for protecting a maternally-derived antibody positive animal against a parvovirus comprising, administering to said animal a parvovirus DNA vaccine, said DNA vaccine comprising a vector, said vector comprising in operable linkage;

at least one isolated nucleotide sequence encoding a parvoviral VP1 polypeptide or a parvoviral VP2 polypeptide, and one or more transcriptional regulatory sequences, wherein said DNA vaccine elicits an immune response in said animal that is protective against parvovirus.

2. The method according to claim 1, wherein said at least one isolated nucleotide sequence encodes a canine parvoviral VP1 polypeptide or a canine parvoviral VP2 polypeptide.

3. The method according to claim 2, wherein said canine parvoviral VP2 polypeptide is selected from canine parvoviral type 2, 2a and 2b.

4. The method according to claim 1, wherein the isolated nucleotide sequence encodes a polypeptide as shown in SEQ ID NO:2.

5. The method according to claim 1, wherein said one or more transcriptional regulatory sequences are of non-parvoviral origin.

6. The method according to claim 5, wherein at least one of said one or more transcriptional regulatory sequences is a cytomegalovirus immediate early promoter.

7. The method according to claim 5, wherein said one or more transcriptional regulatory sequences comprise terminator and polyadenylation sequences.

8. The method according to claim 1, wherein the vector is the plasmid vector which is deposited at the European Collection of Animal Cell Culture, Porton Down, UK under accession no. 97012801.

9. The method according to claim 1, wherein the vector comprises at least one isolated nucleotide sequence encoding a parvoviral VP1 polypeptide and at least one isolated nucleotide sequence encoding a parvoviral VP2 polypeptide.

10. The method according to claim 9, wherein the VP1 and VP2 polypeptides are canine parvoviral polypeptides.

11. A plasmid vector comprising a DNA sequence encoding the VP2 polypeptide of canine parvovirus type 2a, which is deposited at the European Collection of Animal Cell Culture, Porton Down, UK under accession no. 97012801.

12. A canine parvovirus DNA vaccine comprising the plasmid vector deposited with the European Collection of Animal Cell Culture, Porton Down, UK under accession no. 97012801 in a physiologically acceptable medium.

13. A method for protecting a maternally-derived antibody positive animal against canine parvovirus, comprising administering to said animal the DNA vaccine of claim 12.

14. A DNA molecule comprising a vector, at least one isolated nucleotide sequence encoding a parvovirus immunogenic polypeptide, and one or more transcriptional regulatory sequences operably linked to the isolated nucleotide sequence, which will elicit an immune response against parvovirus in a maternally-derived antibody positive animal, wherein said vector is a plasmid vector which is deposited at the European Collection of Animal Cell Culture, Porton Down, UK under accession no. 97012801.

15. A vaccine comprising the DNA molecule of claim 14 in a physiologically acceptable medium.

16. A method for protecting a maternally derived antibody positive animal against a parvovirus, comprising administering to the animal the vaccine of claim 15.

17. The DNA molecule of claim 14, wherein the one or more transcription regulatory sequences are of non-parvoviral origin.

* * * * *